United States Patent [19]

Bianculli

[11] 4,029,797

[45] June 14, 1977

[54] PROCESS OF MAKING COUGH SYRUP WITH MASKED NOSCAPINE

[75] Inventor: Virgil D. Bianculli, Fort Lauderdale, Fla.

[73] Assignee: Fisons Corporation, Bedford, Mass.

[22] Filed: June 20, 1973

[21] Appl. No.: 371,757

[52] U.S. Cl. .............................................. 424/260
[51] Int. Cl.² .................................... A61K 31/485
[58] Field of Search ...................... 424/10, 260, 259

[56] References Cited

UNITED STATES PATENTS 1,048,711  12/1912  Lloyd ................................ 424/260
3,108,041  10/1963  Weiner .............................. 424/260

OTHER PUBLICATIONS

Modern Drug Encyclopedia and Therapeutic Index, 9th Edition, (1963), p. 300.
Modern Drugs, Nov., 1961, p. 754.
Remington's Practice of Pharmacy, 1961, pp. 353–358.
Physician's Desk Reference (PDR), (1971), p. 1214.
Wilson et al., Textbook of Organic Medicinal and Pharmaceutical Chemistry, (1962), 4th Edition, pp. 583–585.
Kigasawa et al., Chemical Abstracts, 62:12987d, (1965).

*Primary Examiner*—Norman A. Drezin
*Attorney, Agent, or Firm*—Richard P. Crowley

[57] ABSTRACT

A process of utilizing the drug noscapine in a palatable cough syrup which masks the characteristic unpalatable taste of the drug comprising the steps of preparing an alkaline carrier and adding noscapine in a form which is a non-acidic solution, but rather in suspension which is finely dispersed.

6 Claims, No Drawings

PROCESS OF MAKING COUGH SYRUP WITH MASKED NOSCAPINE

FIELD OF THE INVENTION

This invention relates to a process and the product of the process for making the taste of noscapine, a cough depressant, in a palatable cough syrup.

BACKGROUND OF THE INVENTION

In the past, the benefits of noscapine have been recognized as an effective antitussive or cough depressant. The problem has been, however, that noscapine in salt form is characterized by a bitter taste, rendering it unpalatable and for the most part unused in liquid form for treating persons with severe coughing spells. In the past, the usual procedure for processing noscapine has been to either use the salt of noscapine, which is a soluble compound in aqueous solution or to acidify the noscapine alkaloid base in order to render it more soluble by conversion to the salt; however, in either event, the characteristic bad taste remains in the resulting mixture or solution.

OBJECTS OF THE PRESENT INVENTION:

The present invention has as a several object the provision of a method of formulation of noscapine to obtain a liquid suspension in which the noscapine is maintained in the alkaloid form, which is relatively tasteless, therefore resulting in a more palatable preparation for use in treating coughs.

GENERAL DESCRIPTION OF THE INVENTION

The method of formulation of this invention comprises the step of adding the noscapine alkaloid base separately from the ingredients of the carrier vehicle until just prior to mixing it in the final resulting mixture; also strictly adhering to an alkaline pH, that is one over seven, to guard against an acidic condition, in which event a salt would form causing an undesirable taste characteristic of noscapine which would render the product of the process unpalatable.

In practice, a syrup vehicle is adjusted with a buffer, such as sodium citrate, to the desired pH above 7 prior to the addition of the noscapine alkaloid; and the buffer serves to maintain the pH throughout the manufacturing process of the life of the product.

EXAMPLE OF THE INVENTION

A. Preparation of Carrier:

As an example of a formulation of a carrier according to this invention, in a stainless steel tank, or first tank, a volume of about 120 liters of Sorbitol solution, 70% by volume, which is a sugar solution, and about 40 liters of a syrup, U.S.P. is mixed with constant agitation, the syrup being about 85% sucrose.

In another vessel, or second tank, 50 liters of deionized water is heated to at about boiling temperature and to this heated water about 266 Gm. of Methylparaben and 135 Gm., or thereabouts, of Propylparaben are mixed and agitated until dissolved for use as preservatives. The preservative is then added to the aforesaid syrup and surgar solution of the first tank and agitated. The resulting mixture is heated to 80° C. whereupon 400 Gm. of sodium citrate is added agitating the mixture until the sodium citrate is completely dissolved to which 400 Gm. of sodium saccharin is added until dissolved and 2,080 Gm. of sodium chloride is then added and mixed until dissolved.

In a separate and third container, which is completely dry, 1,200 Gm. of carboxymethyl cellulose, such as that, known commercially as CMC-7HF, is mixed with 6 liters of glycerin, which is 96% U.S.P. which is mixed with the CMC-7HF well. This third container's content is then mixed with the heated solution of the first and second tank in the first tank or main tank until it is completely dispersed in it.

In a fourth kettle, 112 liters of deionized water is heated to a temperature just below boiling or in the range of between about 90°–95° C. A suspending agent is then added to the 112 liters of heated water and agitated, a suitable suspension agent, being that which is commercially available under the tradename Veegum; a complex magnesium aluminum silicate, a registered trademark of R. T. Vanderbilt Company, Inc. and a predetermined quantity in the order of about 4 kilograms is used. This is maintained at a temperature range of 90°–95° C. for at least 30 minutes or until the mixture has thickened.

The thickened solution of Veegum and water is added to the main tank or main solution and mixed well. A satisfactory coloring agent is then added to the solution, which may consist of 2,000 Ml. of F D & C Fast Lime Shade coloring solution (.5 gm./30 ml.) with agitation.

B. Preparation of Active Ingredient

The noscapine alkaloid which is in powdered from is mixed in the quantity of 1,200 Gm. with 6 L. of glycerin 96% and 2,000 Ml. of a flavoring solution, such as PFC No. 8406 Lemon-Lime Blend.

C. Preparation of Product

The resulting mixture is then mixed and poured into the main tank to the previously mixed carrier. The finished suspension is then brought to a final volume of 400,000 Ml. (400 L. by adding sufficient deionized water) and mixed and allowed to cool to room temperature and comprises the batch which is subdivided for packaging.

IN GENERAL

The composition of the drug of cough suspension includes 15 mg. noscapine per 5 ml. plus color such as lime green in an amount of about 400 liters (440,000 ml.).

|    | Mg./5 ml. |                        | Gm. or ml.   | Kilograms Or Liters |
|----|-----------|------------------------|--------------|---------------------|
| 1. | 15.00 mg. | Noscapine Alkaloid N.F. | 1,200 Gm.    | 1.20 Kg.            |
| 2. | 1.50 ml.  | Sorbitol Solution 70% U.S.P. | 120,000 ml. | 120.00 L.        |
| 3. | 0.50 ml.  | Syrup U.S.P.           | 40,000 ml.   | 40.00 L.            |
| 4. | 0.15 ml.  | Glycerin 96% U.S.P.    | 12,000 ml.   | 12.00 L.            |
| 5. | 5.00 mg.  | Sodium Saccharin N.F.  | 400 Gm.      | 0.40 Kg.            |
| 6. | 5.00 mg.  | Sodium Citrate U.S.P.  | 400 Gm.      | 0.40 Kg.            |
| 7. | 26.00 mg. | Sodium Chloride (Food Grade) | 2,080 Gm. | 2.08 Kg.          |
| 8. | 50.00 mg. | Veegum                 | 4,000 Gm.    | 4.00 Kg.            |

-continued

|  | Mg./5 ml. |  | Gm. or ml. | Kilograms Or Liters |
|---|---|---|---|---|
| 9. | 1.40 ml. | Deionized Water | 112,000 ml. | 112.00 L. |
| 10. | 15.00 mg. | Sodium Carboxymethyl (Cellulose (CMC-7HF) | 1,200 Gm. | 1.20 Kg. |
| 11. | .025 ml. | F D & C Fast Lime Shade (Color) (.5 Gm./30 ml.) | 2,000 ml. | 2.00 L. |
| 12. | .025 ml. | PFC No. 8406 Lemon-Lime Blend (Flavor) | 2,000 ml. | 2.00 L. |
| 13. | 3.33 mg. | Methylparaben U.S.P. | 266 Gm. | 0.26 Kg. |
| 14. | 1.67 mg. | Propylparaben U.S.P. | 134 Gm. | 0.13 Kg. |
| 15. | q.s. | Deionized Water q.s. Ad. | 400,000 ml. | 400.00 L. |

It has been found that the effectiveness of the product of the process is in the range of the effectiveness of codeine as an antitussive agent while at the same time permitting reflex coughing to continue and for doses to be administered without side effects, similar to that of narcotics, the cough syrup effectively masks the characteristics bad taste of noscapine.

What is claimed:

1. A method of preparing a palatable-tasting cough syrup formulation containing noscapine, which method comprises:
   a. preparing an aqueous liquid syrup-type carrier solution for the noscapine, which carrier includes a buffer to maintain the pH of the liquid carrier above a pH of 7 at all times; and
   b. mixing alkaloid noscapine in the absence of noscapine in salt form with the liquid carrier to form a fine suspension of the alkaloid noscapine therein, thereby providing a palatable-tasting liquid formulation of suspended noscapine essentially free of any bitter-tasting noscapine salts.

2. The method of claim 1 wherein the buffer is sodium citrate.

3. The method of claim 1 which includes diluting the liquid formulation so prepared with water to provide a cough syrup containing a cough-depressant amount of the suspended noscapine.

4. The method of claim 1 wherein the aqueous liquid carrier comprises sucrose, sorbitol, a preservative, carboxymethyl cellulose, glycerin and a suspending agent.

5. The method of claim 1 wherein the noscapine is powdered form is mixed with a glycerine-containing solution, and the said solution is admixed into the carrier solution.

6. The method of claim 1 wherein the liquid carrier solution is prepared by mixing a water solution of sorbitol and a syrup with a water solution of methylparaben and propylparaben and sodium citrate as a buffer, and heating the solution, and, thereafter, adding to the heated mixed solution a water solution with carboxymethyl cellulose, and, thereafter, adding to the mixed solution a heated water solution containing a suspending agent, and mixing into the carrier solution so prepared a solution of glycerin and a flavoring solution in which is suspended powdered noscapine in alkaloid form.

* * * * *